(12) United States Patent
Uchida et al.

(10) Patent No.: US 10,266,501 B2
(45) Date of Patent: Apr. 23, 2019

(54) CRYSTAL FORMS OF 6-BROMO-3-HYDROXY-2-PYRAZINE-CARBOXAMIDE

(71) Applicant: FUJIFILM Toyama Chemical Co., Ltd., Chuo-ku (JP)

(72) Inventors: Tetsuro Uchida, Toyama (JP); Sayuri Uehara, Toyama (JP); Takayoshi Tsuzuki, Toyama (JP); Yusuke Okubo, Toyama (JP); Yuta Kobayashi, Toyama (JP); Yu Koseki, Toyama (JP)

(73) Assignee: FUJIFILM Toyama Chemical Co., Ltd., Chuo-ku (JP)

( * ) Notice: Subject to any disclaimer, the term of this patent is extended or adjusted under 35 U.S.C. 154(b) by 0 days.

(21) Appl. No.: 15/580,731

(22) PCT Filed: Jun. 8, 2016

(86) PCT No.: PCT/JP2016/067114
§ 371 (c)(1),
(2) Date: Dec. 8, 2017

(87) PCT Pub. No.: WO2016/199824
PCT Pub. Date: Dec. 15, 2016

(65) Prior Publication Data
US 2018/0141920 A1 May 24, 2018

Related U.S. Application Data

(60) Provisional application No. 62/172,958, filed on Jun. 9, 2015.

(51) Int. Cl.
*C07D 241/24* (2006.01)
(52) U.S. Cl.
CPC .............................. *C07D 241/24* (2013.01)

(58) Field of Classification Search
CPC .................................................... C07D 241/24
USPC ........................................................... 544/409
See application file for complete search history.

(56) References Cited

U.S. PATENT DOCUMENTS

| 8,835,636 B2 * | 9/2014 | Hara | C07D 241/16 544/409 |
|---|---|---|---|
| 2003/0130213 A1 | 7/2003 | Egawa et al. | |
| 2010/0286394 A1 | 11/2010 | Takamatsu et al. | |

FOREIGN PATENT DOCUMENTS

| JP | 2010-241806 A | 10/2010 |
|---|---|---|
| JP | 2011-6404 A | 1/2011 |
| JP | 5559604 B2 | 7/2014 |
| JP | 5739618 B2 | 6/2015 |
| WO | 01/60834 A1 | 8/2001 |
| WO | 2009/041473 A1 | 4/2009 |

OTHER PUBLICATIONS

International Search Report dated Aug. 16, 2016 in PCT/JP2016/067114 filed Jun. 8, 2016.
"6th edition Kagaku Benran Oyo Kagaku Hen I", edited by CSJ: The Chemical Society of Japan, Jan. 30, 2003, 3 total pages.
Mitsutaka Kitamura, "Mechanism of polymorphism and control of polymorphic crystallization", Industrial Publishing & Consulting, Inc., Aug. 10, 2010, 4 total pages.

* cited by examiner

*Primary Examiner* — Douglas M Willis
(74) *Attorney, Agent, or Firm* — Oblon, McClelland, Maier & Neustadt, L.L.P.

(57) ABSTRACT

The purpose of the present invention is to provide a method for producing 6-bromo-3-hydroxy-2-pyrazinecarboxamide in which the content ratio of impurities is reduced. This production method includes a step of obtaining 6-bromo-3-hydroxy-2-pyrazinecarboxamide crystal having diffraction angles expressed in degrees 2θ of 5.5, 20.1, 23.7, 26.7, 27.5, and 28.1° and/or diffraction angles expressed in degrees 2θ of 7.1, 21.4, 25.2, 25.7, 27.1, and 28.8° in powder X-ray diffraction.

4 Claims, 5 Drawing Sheets

INFRARED ABSORPTION SPECTRUM (ATR METHOD) OF
TYPE-A CRYSTAL OF COMPOUND D

TYPE-A CRYSTAL OF COMPOUND D

INFRARED ABSORPTION SPECTRUM (ATR METHOD) OF
TYPE-B CRYSTAL OF COMPOUND D

TYPE-B CRYSTAL OF COMPOUND D

INFRARED ABSORPTION SPECTRUM (ATR METHOD) OF
TYPE-C CRYSTAL OF COMPOUND D

TYPE-C CRYSTAL OF COMPOUND D

INFRARED ABSORPTION SPECTRUM (ATR METHOD) OF
ANHYDROUS FORM OF COMPOUND C

ANHYDROUS FORM OF COMPOUND C

INFRARED ABSORPTION SPECTRUM (ATR METHOD) OF
HYDRATE OF COMPOUND C

HYDRATE OF COMPOUND C

CRYSTAL FORMS OF 6-BROMO-3-HYDROXY-2-PYRAZINE-CARBOXAMIDE

CROSS-REFERENCE TO RELATED APPLICATIONS

The present application is a National Stage of and claims the benefit of priority to International Application No. PCT/JP2016/067114, filed Jun. 8, 2016, which is based upon and claims the benefit of priority to U.S. Provisional Application No. 62/172,958 filed Jun. 9, 2015.

TECHNICAL FIELD

The present invention relates to a crystal of 6-bromo-3-hydroxy-2-pyrazinecarboxamide, and a production method thereof. The present invention also relates to an anhydrous form of 3-hydroxy-2-pyrazinecarboxamide. The present invention further relates to 6-fluoro-3-hydroxy-2-pyrazinecarboxamide having a decreased content ratio of 3-hydroxy-2-pyrazinecarboxamide.

BACKGROUND ART

6-Fluoro-3-hydroxy-2-pyrazinecarboxamide (hereinafter, sometimes referred to as "compound A".) is useful for treatments such as prevention and therapy of infection due to the influenza virus. Compound A is produced from, for example, 6-fluoro-3-hydroxy-2-pyrazinecarbonitrile (hereinafter, sometimes referred to as "compound B") (Patent Documents 1 and 2).

Meanwhile, compound B is produced from, for example, 6-bromo-3-hydroxy-2-pyrazinecarboxamide (hereinafter, sometimes referred to as "compound D"), which is obtained by brominating 3-hydroxy-2-pyrazinecarboxamide (hereinafter, sometimes referred to as "compound C") (Patent Document 3).

In addition, compound C is produced from, for example, aminomalonamide (Patent Document 4).

PRIOR ART DOCUMENTS

Patent Documents

Patent Document 1: International Publication No. WO2009/041473pamphlet
Patent Document 2: International Publication No. WO01/60834pamphlet
Patent Document 3: JP 5559604 B
Patent Document 4: JP 5739618 B

SUMMARY OF INVENTION

Technical Problem

There is a need to provide high-purity compound A when compound A is used as an active pharmaceutical ingredient in a medicine.

The present inventors have made studies, and as a result, have found that compound A includes compound C as an impurity.

An object of the present invention is to provide compound D having a decreased content ratio of impurities, for use in production of high-purity compound A, and a method for producing compound D.

Solution to Problem

The present inventors have conducted intensive studies in view of such circumstances, and as a result, have found that compound C can exist in an anhydrous form and compound D has crystal polymorphs. The inventors have also found that the reaction yield is increased and compound D having a decreased content ratio of compound C is obtained by decreasing the content ratio of water in the reaction system in a bromination reaction step of compound C. The inventors have further found that, in the bromination reaction step of compound C, compound D having an extremely low content ratio of compound C can be produced by once isolating crystalline compound D. The inventors have then found compound A having an extremely low content ratio of compound C by using the resulting compound D, leading to completion of the present invention.

[Formula 1]

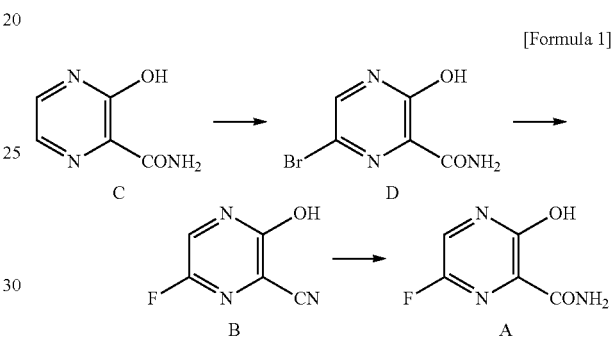

The present invention provides the following.

[1] A method for producing compound D, comprising: (1) preparing a suspension comprising compound C and a solvent; and (2) adding bromine to the suspension obtained in step (1); wherein the content ratio of water included in the suspension obtained in step (1) is less than 5% (w/w) relative to compound C; and the content ratio of compound C included in compound D is less than 300 ppm.

[2] The production method according to [1], further comprising: (3) obtaining crystalline compound D (hereinafter, sometimes referred to as "type-A crystals"), the crystal having diffraction angles of 5.5, 20.1, 23.7, 26.7, 27.5 and 28.1° in terms of 2θ in powder X-ray diffraction.

[3] The production method according to [1], further comprising: (3) obtaining crystalline compound D, the crystals having diffraction angles of 5.5, 20.1, 23.7, 26.7, 27.5 and 28.1° in terms of 2θ in powder X-ray diffraction; (4) reacting the crystal obtained in step (3) with a base to obtain a salt of compound D; and (5) reacting the salt obtained in step (4) with an acid, to obtain crystalline compound D (hereinafter, sometimes referred to as "type-B crystals"), the crystal having diffraction angles of 7.1, 21.4, 25.2, 25.7, 27.1 and 28.8° in terms of 2θ in powder X-ray diffraction.

[4] The production method according to [3], wherein the base for use in step (4) is at least one base selected from sodium hydroxide, sodium hydrogen carbonate and potassium hydroxide, and the acid for use in step (5) is at least one acid selected from hydrochloric acid, nitric acid and sulfuric acid.

[5] The production method according to any one of [1] to [4], wherein compound C for use in step (1) is an anhydrous form of compound C.

[6] A method for producing compound D, comprising: (4) reacting crystalline compound D, the crystal having diffraction angles of 5.5, 20.1, 23.7, 26.7, 27.5 and 28.1° in terms of 2θ in powder X-ray diffraction with a base to obtain a salt of compound D, and (5) reacting the salt obtained in step (4) with an acid to obtain crystalline compound D, the crystal having diffraction angles of 7.1, 21.4, 25.2, 25.7, 27.1 and 28.8° in terms of 2θ in powder X-ray diffraction.

[7] The production method according to [6], wherein the base for use in step (4) is at least one base selected from sodium hydroxide, sodium hydrogen carbonate and potassium hydroxide, and the acid for use in step (5) is at least one acid selected from hydrochloric acid, nitric acid and sulfuric acid.

[8] Crystalline compound D, the crystals having diffraction angles of 5.5, 20.1, 23.7, 26.7, 27.5 and 28.1° in terms of 2θ in powder X-ray diffraction, wherein the content ratio of compound C included in compound D is less than 300 ppm.

[9] Crystalline compound D, the crystals having diffraction angles of 7.1, 21.4, 25.2, 25.7, 27.1 and 28.8° in terms of 2θ in powder X-ray diffraction, wherein the content ratio of compound C included in compound D is less than 300 ppm.

[10] An anhydrous form of compound C.

[11] An anhydrous crystal of compound C, the crystals having diffraction angles of 11.9, 13.2, 23.9 and 26.7° in terms of 2θ in powder X-ray diffraction.

[12] Compound A, wherein the content ratio of compound C is less than 5 ppm.

The present invention further provides the following.

[A] Crystalline compound D (hereinafter, sometimes referred to as "type-C crystals"), the crystals having diffraction angles of 16.7, 23.7, 26.4, 26.7, 29.0 and 31.5° in terms of 2θ in powder X-ray diffraction, wherein the content ratio of compound C included in compound D is less than 300 ppm.

[B] A pharmaceutical composition including compound A wherein the content ratio of compound C is less than 5 ppm.

ADVANTAGEOUS EFFECTS OF INVENTION

The production method of the present invention is useful as a method for producing compound D having a decreased content ratio of compound C, for use in production of high-purity compound A.

Type-A crystals of compound D of the present invention are useful as an intermediate for production of high-quality compound A.

Type-B crystals of compound D of the present invention are useful as an intermediate for production of high-quality compound A.

An anhydrous form of compound C of the present invention is useful as a raw material for production of compound D having a decreased content ratio of compound C.

Compound A having a decreased content ratio of compound C, of the present invention, is useful as an active pharmaceutical ingredient of a high-quality medicine.

DESCRIPTION OF EMBODIMENTS

Figure 1:
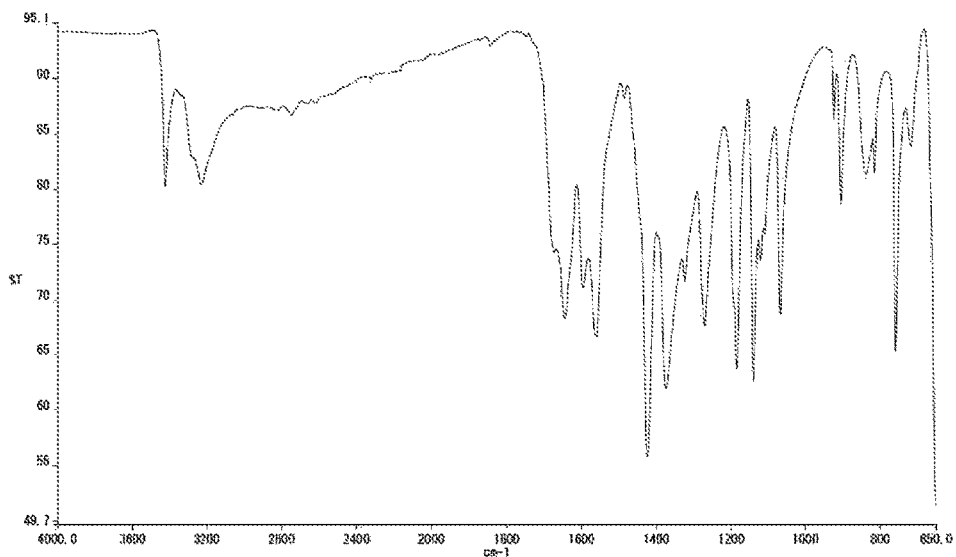
FIG. 1 illustrates one example of the infrared absorption spectrum (ATR method) of type-A crystals of compound D.

Hereinafter, the present invention will be described in detail.

The symbol "%" used herein means "% by mass", unless particularly noted.

The following terms have respective meanings described below, unless particularly noted.

The term "compound A" means 6-fluoro-3-hydroxy-2-pyrazinecarboxamide.

The term "compound B" means 6-fluoro-3-hydroxy-2-pyrazinecarbonitrile.

The term "compound C" means 3-hydroxy-2-pyrazinecarboxamide.

The term "compound D" means 6-bromo-3-hydroxy-2-pyrazinecarboxamide.

It is to be noted that compounds A to D each have tautomers. The present invention encompasses such tautomers.

Examples of aliphatic hydrocarbons include pentane, hexane, cyclohexane or decahydronaphthalene.

Examples of halogenated hydrocarbons include methylene chloride, chloroform or dichloroethane.

Examples of alcohols include methanol, ethanol, propanol, 2-propanol, butanol or 2-methyl-2-propanol.

Examples of ethers include diethyl ether, diisopropyl ether, dioxane, tetrahydrofuran, anisole, ethylene glycol dimethyl ether, di ethylene glycol dimethyl ether or diethylene glycol diethyl ether.

Examples of ketones include acetone, 2-butanone or 4-methyl-2-pentanone.

Examples of esters include methyl acetate, ethyl acetate, propyl acetate or butyl acetate.

Examples of amides include N,N-dimethylformamide, N,N-dimethylacetamide or 1-methyl-2-pyrrolidone.

Examples of nitriles include acetonitrile or propiononitrile.

Examples of sulfoxides include dimethylsulfoxide.

Examples of aromatic hydrocarbons include benzene, toluene or xylene.

In general, the wavenumber (cm$^{-1}$) value in an infrared absorption spectrum (ATR method) can have a margin of error within a range of ±2 cm$^{-1}$. Accordingly, the designation "wavenumber Y" used in the present invention means "wavenumber ((Y−2) to (Y+2)) cm$^{-1}$", unless particularly noted. Accordingly, the present invention encompasses not only crystals where the wavenumbers of absorption peaks in an infrared absorption spectrum (ATR method) are completely matched, but also crystals where the wavenumbers of absorption peaks are matched with a margin of error within a range of ±2 cm$^{-1}$.

In general, the diffraction angle (2θ) in powder X-ray diffraction can have a margin of error within a range of ±0.2°. Accordingly, the designation "diffraction angle (2θ) of X°" used in the present invention means "diffraction angle (2θ) of ((X−0.2) to (X+0.2))°", unless particularly noted. Accordingly, the present invention encompasses not only crystals where the diffraction angles in powder X-ray diffraction are completely matched, but also crystals where the diffraction angles are matched with a margin of error within a range of ±0.2°.

[Hydrate of Compound C]

Compound C can be produced according to any method described in the Journal of Medicinal Chemistry (J. Med. Chem.), vol. 26, pp. 283 to 286 (1983) or JP 2010-241806 A. Such a method is a method for precipitating compound C in an aqueous solvent.

Compound C is hardly soluble in various organic solvents, and is difficult to isolate by an operation such as extraction. Therefore, compound C is isolated according to any method such as neutralization crystallization in an aqueous solvent.

The present inventors have made studies, and as a result, have found that compound C isolated from an aqueous solvent is a hydrate.

[Anhydrous Form of Compound C]

An anhydrous form of compound C is a novel compound and has not been previously known at all.

An anhydrous crystal of compound C has diffraction angles of 11.9, 13.2, 23.9 and 26.7° in terms of 2θ in powder X-ray diffraction.

In addition, the anhydrous crystal of compound C has characteristic peaks at 1710, 1678 and 1643 cm$^{-1}$ in the infrared absorption spectrum.

The anhydrous form of compound C can be produced by, for example, heating and stirring a suspension of a hydrate of compound C.

The solvent for use in such a reaction is not particularly limited as long as it has no effect on the reaction. Examples thereof include alcohols, ethers, amides and sulfoxides, and these may be used as a mixture thereof. Examples of the solvent preferably include amides, N,N-dimethylformamide and N,N-dimethylacetamide are more preferable, and N,N-dimethylformamide is further preferable.

The amount of solvent to be used may be 1 to 10 times (v/w) and is preferably 2 to 4 times (v/w) the amount of hydrate of compound C.

The reaction temperature may be 40 to 100° C. and is preferably 60 to 80° C.

The reaction time may be 5 minutes to 50 hours and is preferably 5 minutes to 5 hours.

In the reaction, a base may also be added.

Examples of the base used include organic bases such as diethylamine, diisopropylamine, triethylamine, pyridine, picoline and lutidine, pyridine being preferable.

The amount of the base to be used may be 1 to 3 times by mole and is preferably 1.5 to 2.5 times by mole the amount of hydrate of compound C.

[Compound D]

Compound D can be produced by, for example, the method described in Patent Document 3.

Patent Document 3 describes the reaction time and the production yield in the bromination reaction of compound C.

The rate of bromination after 1 hour from the start of the reaction reaches a maximum value, the value being 82 to 86%.

Compound C has been previously known as a hydrate. Therefore, a hydrate of compound C has been used for the bromination reaction of compound C. As described below, when the bromination reaction is performed using a hydrate of compound C, the content ratio of compound C included in the resulting compound D is 300 ppm or more.

It is difficult to produce, from a hydrate of compound C, compound D having a content ratio of compound C of less than 300 ppm.

[Type-A Crystals of Compound D]

Type-A crystals of compound D have diffraction angles of 5.5, 20.1, 23.7, 26.7, 27.5 and 28.1° in terms of 2θ in powder X-ray diffraction.

In addition, type-A crystals of compound D have characteristic peaks at 1673, 1644, 1595 and 1560 cm$^{-1}$ in the infrared absorption spectrum.

Type-A crystals of compound D can be obtained by, for example, adding a poor solvent to a reaction mixture obtained in a bromination step of compound C.

Examples of a poor solvent include aliphatic hydrocarbons, halogenated hydrocarbons, alcohols, ethers, esters, ketones, nitriles, aromatic hydrocarbons and water, and these may be used as a mixture thereof. Examples of a poor solvent preferably include alcohols, ethers and water; ethanol, propanol, 2-propanol, butanol and water being more preferable.

The temperature at which the poor solvent is added may be 10 to 50° C. and is preferably 20 to 50° C., more preferably 30 to 50° C.

Patent Document 3 describes a production method including adding water at 60 to 70° C. to a reaction mixture obtained in a bromination step of compound C. The present inventors have found that, when the temperature at addition is 60 to 70° C., the resulting crystals are type-B crystals. The inventors have also found that, when the temperature at addition is 20 to 50° C., the resulting crystals are type-A crystals.

Type-A crystals of compound D may include type-B crystals of compound D, described below. They may also include type-C crystals of compound D.

As described above, when the bromination reaction is performed using a hydrate of compound C, the content ratio of compound C included in the resulting type-A crystals of compound D is 300 ppm or more.

[Type-A Crystals of Compound D Having a Content Ratio of Compound C of Less than 300 ppm]

Type-A crystals of compound D having a content ratio of compound C of less than 300 ppm, can be obtained by, for example, providing a suspension including compound C and a solvent so that the content ratio of water included in the suspension is less than 5% (w/w) relative to compound C, conducting a bromination reaction of compound C, and adding a poor solvent to the resulting reaction mixture.

Examples of a poor solvent include aliphatic hydrocarbons, halogenated hydrocarbons, alcohols, ethers, esters, ketones, nitriles, aromatic hydrocarbons and water, and these may be used as a mixture thereof. Examples of a poor solvent preferably include alcohols, ethers and water; ethanol, propanol, 2-propanol, butanol and water being more preferable.

The temperature at which the poor solvent is added may be 10 to 50° C. and is preferably 30 to 50° C.

Type-A crystals of compound D may also include type-B crystals of compound D. They may also include type-C crystals of compound D.

The content ratio of compound C may be less than 300 ppm, and is preferably less than 200 ppm, more preferably less than 100 ppm, further preferably less than 50 ppm.

Type-A crystals of compound D have the property of allowing compound C contained in compound D to be effectively removed. Therefore, compound D having a low content of compound C can be produced by once isolating type-A crystals of compound D in a step of producing compound D from compound C.

When type-A crystals of compound D are left to stand at room temperature, they are converted into type-C crystals of compound D, described below. It is difficult to store type-A crystals of compound D for a long period.

[Type-B Crystals of Compound D]

Type-B crystals of compound D have diffraction angles of 7.1, 21.4, 25.2, 25.7, 27.1 and 28.8° in terms of 2θ in powder X-ray diffraction.

In addition, type-B crystals of compound D have characteristic peaks at 1660, 1644 and 1581 $cm^{-1}$ in the infrared absorption spectrum.

Type-B crystals of compound D can be produced by, for example, the method described in Patent Document 3. Specifically, they can be obtained by adding a poor solvent to the reaction mixture obtained in the bromination step of compound C.

Examples of a poor solvent include aliphatic hydrocarbons, halogenated hydrocarbons, alcohols, ethers, esters, ketones, nitriles, aromatic hydrocarbons and water, and these may be used as a mixture thereof. Examples of a poor solvent preferably include alcohols, ethers and water; ethanol, propanol, 2-propanol, butanol and water being more preferable.

The temperature at which the poor solvent is added may be 50 to 90° C., and is preferably 50 to 70° C., more preferably 60 to 70° C.

Type-B crystals of compound D can also be obtained by, for example, dissolving type-A crystals or type-C crystals of compound D in N,N-dimethylformamide, and thereafter adding a poor solvent thereto.

Examples of a poor solvent include aliphatic hydrocarbons, halogenated hydrocarbons, alcohols, ethers, esters, ketones, nitriles, aromatic hydrocarbons and water, and these may be used as a mixture thereof. Examples of a poor solvent preferably include alcohols, ethers and water; ethanol, propanol, 2-propanol, butanol and water being more preferable.

The temperature at which the poor solvent is added may be 50 to 90° C. and is preferably 50 to 70° C.

Furthermore, type-B crystals of compound D can also be obtained by a production method, described below, by use of an acid and a base.

Type-B crystals of compound D may include type-A crystals of compound D. They may also include type-C crystals of compound D.

[Type-B Crystals of Compound D Having a Content Ratio of Compound C of Less than 300 ppm]

Type-B crystals of compound D having a content ratio of compound C of less than 300 ppm can be obtained by, for example, using type-A crystals of compound D having a content ratio of compound C of less than 300 ppm according to a production method described below.

The content ratio of compound C may be less than 300 ppm, and is preferably less than 200 ppm, more preferably less than 100 ppm, further preferably less than 50 ppm, particularly preferably less than 20 ppm.

Type-B crystals of compound D have the property of allowing compound C contained in compound D to be effectively removed. Therefore, type-B crystals of compound D can be once isolated in the step of producing compound D from compound C, thereby producing compound D having a low content ratio of compound C.

In addition, type-B crystals of compound D are excellent in storage stability and are useful as an intermediate for production of high-quality compound A.

[Type-C Crystals of Compound D]

Type-C crystals of compound D have diffraction angles of 16.7, 23.7, 26.4, 26.7, 29.0 and 31.5° in terms of 2θ in powder X-ray diffraction.

In addition, type-C crystals of compound D have characteristic peaks at 1664 and 1568 $cm^{-1}$ in the infrared absorption spectrum.

Type-C crystals of compound D can be produced by, for example, leaving type-A crystals of compound D to stand at room temperature.

The standing time may be one week to one year.

Type-C crystals of compound D having a decreased content ratio of compound C can be produced by using type-A crystals of compound D having a decreased content ratio of compound C.

[Compound A Having a Decreased Content Ratio of Compound C]

Compound D produced in the production method of the present invention can be used to produce compound A having a decreased content ratio of compound C. Specifically, type-B crystals of compound D having a content ratio of compound C of less than 300 ppm can be used to produce compound A having a content ratio of compound C of less than 5 ppm.

Next, the production method of the present invention will be described.

[Production Method 1]

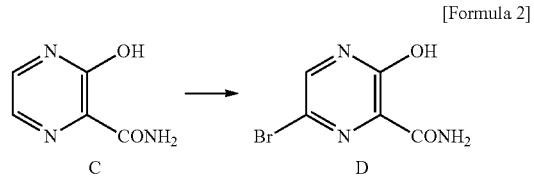

[Formula 2]

(1)

Step (1) is a step of preparing a suspension including compound C and a solvent.

Examples of the solvent include amides and sulfoxides, and these may be used as a mixture thereof. Examples of the solvent preferably include amides, N,N-dimethylformamide and N,N-dimethylacetamide being preferable, and N,N-dimethylformamide being further preferable.

The amount of solvent to be used may be 1 to 10 times (v/w) and is preferably 2 to 4 times (v/w) the amount of compound C.

Compound C has been previously known as a hydrate.

The content ratio of water included in the suspension in a bromination step of compound C may be less than 5% (w/w) relative to compound C, and is preferably less than 3% (w/w), further preferably less than 2% (w/w), particularly preferably less than 1% (w/w).

Examples of the method for preparing a suspension having a content ratio of water of less than 5% (w/w) include:

(1-a) a method of using an anhydrous form of compound C, and/or (1-b) a method of decreasing the water content ratio in the reaction system.

(1-a)

An anhydrous form of compound C can be produced according to, for example, the above production method or any method described in the Examples.

An anhydrous form of compound C may also be produced in the reaction system.

An anhydrous form of compound C may be isolated, but need not be isolated.

(1-b)

Examples of the method for decreasing the content ratio of water in the reaction system include performing a reaction with a dehydrating agent, heating and stirring, and/or performing azeotropic dehydration, after preparation of a suspension including a hydrate of compound C and a solvent.

Examples of the dehydrating agent include silica gel, activated alumina and molecular sieve.

Examples of the solvent for use in azeotropic dehydration include alcohols such as ethanol, propanol, 2-propanol, butanol, isobutyl alcohol, 2-butanol and tert-butanol; ethers such as 1,2-dimethoxyethane, diisopropyl ether, tetrahydrofuran and dioxane; hydrocarbons such as cyclohexane, benzene, toluene and xylene; acetonitrile; pyridine; and nitromethane.

(2)

Step (2) is a step of adding bromine to the suspension obtained in step (1).

The amount of bromine to be used may be 1 to 10 times by mole and is preferably 1.0 to 5.0 times by mole, more preferably 1.0 to 1.5 times by mole, the amount of compound C.

The reaction temperature may be 0 to 150° C. and is preferably 50 to 100° C.

The reaction time may be 5 minutes to 50 hours and is preferably 5 minutes to 5 hours.

By decreasing the content ratio of water included in the suspension to less than 5% (w/w), the reaction yield increases, and compound D having a decreased content ratio of compound C can be produced.

The production method of the present invention preferably further includes the following steps.

(3)

Step (3) is a step of obtaining type-A crystals of compound D.

Type-A crystals of compound D have the property of allowing compound C contained in compound D to be effectively removed. Therefore, compound D having a low content ratio of compound C can be produced by once isolating type-A crystals of compound D in the step of producing compound D from compound C.

Type-A crystals of compound D can be obtained by, for example, adding a poor solvent to the reaction mixture obtained in step (2).

Examples of a poor solvent include aliphatic hydrocarbons, halogenated hydrocarbons, alcohols, ethers, esters, ketones, nitriles, aromatic hydrocarbons and water, and these may be used as a mixture thereof. Examples of a poor solvent preferably include alcohols, ethers, aromatic hydrocarbons and water; ethanol, propanol, 2-propanol, butanol, toluene and water being preferable.

The temperature at which the poor solvent is added may be 10 to 50° C. and is preferably 30 to 50° C.

Type-A crystals of compound D may include type-B crystals of compound D. They may also include type-C crystals of compound D.

(4)

Step (4) is a step of reacting the crystal obtained in step (3) with a base to obtain a salt of compound D.

An example of the solvent for use in this reaction is water.

The amount of the solvent to be used is not particularly limited, and may be 1 to 10 times (v/w) and is preferably 1 to 5 times (v/w) the amount of crystals of compound D.

Examples of the base for use in this reaction include sodium hydroxide, sodium hydrogen carbonate and potassium hydroxide, sodium hydroxide and sodium hydrogen carbonate being preferable, and sodium hydroxide being more preferable.

The amount of base to be used may be 1 to 10 times by mole and is preferably 1.0 to 5.0 times by mole, more preferably 1.0 to 1.5 times by mole, the amount of the crystal of compound D.

The reaction temperature may be 0 to 100° C. and is preferably 5 to 50° C.

The reaction time may be 5 minutes to 50 hours and is preferably 5 minutes to 5 hours.

The salt of compound D may be isolated, but is preferably used in the next step without isolation.

(5)

Step (5) is a step of reacting the salt obtained in step (4) with an acid to obtain type-B crystals of compound D.

Type-B crystals of compound D have the property of allowing compound C contained in compound D to be effectively removed. Therefore, compound D having a low content ratio of compound C can be produced by isolating type-B crystals of compound D in the step of producing compound D from compound C.

Type-B crystals of compound D can be obtained by reacting the salt obtained in step (4) with an acid.

An example of the solvent for use in this reaction is water.

The amount of the solvent to be used is not particularly limited, and may be 1 to 10 times (v/w) and is preferably 1 to 5 times (v/w) the amount of salt of compound D.

Examples of the acid for use in this reaction include hydrochloric acid, nitric acid and sulfuric acid, hydrochloric acid being preferable.

The amount of the acid to be used may be 1 to 10 times by mole, preferably 1.0 to 5.0 times by mole, more preferably 1.0 to 1.5 times by mole the amount of salt of compound D.

The reaction temperature may be 50 to 90° C. and is preferably 50 to 70° C.

The reaction time may be 5 minutes to 50 hours and is preferably 5 minutes to 5 hours.

Type-B crystals of compound D may include type-A crystals of compound D. They may also include type-C crystals of compound D.

Type-B crystals of compound D obtained by the above production method are crystals having a content ratio of compound C of less than 300 ppm. The crystals can be used to thereby produce compound A having a content ratio of compound C of less than 5 ppm.

Next, the present invention will be described with reference to Test Examples, Reference Examples and Examples, but the present invention is not intended to be limited thereto.

The water content was measured with a CA-100 water content measurement apparatus (Mitsubishi Chemical Analytech Co., Ltd.).

The infrared absorption spectrum was measured with a Spectrum One (PerkinElmer Co., Ltd.).

The measurement conditions of high-performance liquid chromatography are shown below.

Detector: ultraviolet absorption photometer
Measurement wavelength: 254 nm
Column: Develosil ODS-HG-5, inner diameter 4.6 mm X length 150 mm
Column temperature: room temperature
Mobile phase: 21% acetonitrile buffer solution (0.05 mol/L acetic acid, 0.025 mol/L triethylamine)
Flow rate: 1 mL/min The measurement conditions of powder X-ray diffraction are shown below.

X-ray used: CuKα
Voltage applied: 40 kV
Current drawn: 40 mA
Scanning range: 2θ=2 to 40°
Measurement time: 20 minutes

TEST EXAMPLE 1

The relationship between the water content value in the reaction system and the remaining ratio of compound C in the bromination step of compound C was examined.

Water (0, 0.1, 0.31, 0.50 or 1.0 mL) and pyridine (9.3 mL) were added to a suspension of an anhydrous form of compound C (10.0 g) in N,N-dimethylformamide (25 mL); bromine (13.8 g) was added thereto at 70 to 80° C. The reaction mixture was stirred at that temperature for 2 hours, and toluene (5 mL) was added thereto at 60 to 70° C. The reaction mixture was cooled to 47° C., and water (30 mL) was added thereto, and thereafter the resulting mixture was cooled to 10° C. A solid was collected by filtration to obtain compound D.

The form of the crystals of compound D was determined based on the infrared absorption spectrum.

The content ratio of compound C included in compound D was measured by HPLC.

The results are shown below.

TABLE 1

| Compound C | Amount of water added | Unreacted compound C | | Yield | | Content ratio of compound C |
|---|---|---|---|---|---|---|
| (g) | (mL) | (%)*1 | (%) | (%) | Compound D | (ppm) |
| 1 | 10.0 | 0.00 | 0.0 | 1.7 | 68 | Type-A crystals | 50 |
| 2 | 10.0 | 0.10 | 1.0 | 3.6 | 68 | Type-A crystals | 250 |
| 3 | 10.0 | 0.31 | 3.1 | 4.5 | 70 | Type-A crystals | 290 |
| 4 | 10.0 | 0.50 | 5.0 | 6.3 | 69 | Type-A crystals | 360 |
| 5 | 10.0 | 1.00 | 10.0 | 15.8 | 65 | Type-A crystals | 500 |

*1 % by mass relative to compound C

When the amount of water added was 10% (No. 5), the ratio of unreacted compound C in the reaction mixture was 15.8%, the yield was 65%, and the content ratio of compound C included in the resulting compound D was 500 ppm.

Meanwhile, as the amount of water added decreased, the content ratio of unreacted compound C and the content ratio of compound C decreased.

The amount of water added and the content ratio of compound C included in compound D correlated with each other. It is clear that, when a hydrate of compound C is used as a starting material, the content ratio of compound C included in compound D is high.

It was found that the reaction yield increases and compound D having a decreased content ratio of compound C is obtained by decreasing the content ratio of water in the reaction system.

TEST EXAMPLE 2

Type-A crystals, type-B crystals or type-C crystals of compound D were packed in double plastic bags and stored under conditions of 60° C. temperature and 75% relative humidity. Sampling was performed over time, and the crystal form was determined by infrared absorption spectrum measurement. The results are shown below.

TABLE 2

|  | Type-A crystals | Type-B crystals | Type-C crystals |
|---|---|---|---|
| Initiation of test | A | B | C |
| 4 weeks | A | B | C |
| 8 weeks | A + C (major) | B | C |

Type-A crystals were changed to type-C crystals. Type-B crystals and type-C crystals were not changed.

Type-B crystals and type-C crystals were stable.

TEST EXAMPLE 3

Compound D having a high content ratio of compound C was used to examine the relationship between the form of the crystals of compound D and the remaining ratio of compound C.

Compound D of Reference Example 2 was used as a test compound. The content ratio of compound C included in the test compound was 5039 ppm.

The test compound was dissolved in N,N-dimethylformamide while being heated, and then water was added thereto to produce crystals of compound D (Examples 2 and 3).

The content ratio of compound C included in compound D was measured by HPLC.

The results are shown below.

TABLE 3

| | (Raw material) | (Product) | | |
|---|---|---|---|---|
| | Content ratio of compound C (ppm) | Crystal form | Content ratio of compound C (ppm) | Rate of removal (%) |
| Example 2 | 5039 | Type-A crystals | 54 | 99 |
| Example 3 | 5039 | Type-B crystals | 1164 | 77 |

The removal ratio of compound C with respect to type-A crystals was 99%, and the removal ratio with respect to type-B crystals was 77%. Type-A crystals and type-B crystals allowed compound C included in compound D to be effectively removed. In particular, type-A crystals allowed compound C to be effectively removed.

REFERENCE EXAMPLE 1

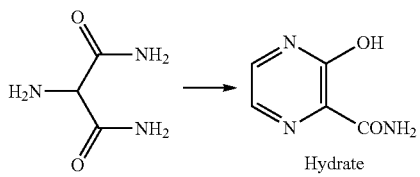 [SMILES: NC(=O)C(N)C(N)=O ; NC(=O)c1nccnc1O]
Hydrate

The Example was performed according to the method in Example 1 of JP 2010-241806 A.

To obtain a phosphate buffer, 13.7 g of sodium hydroxide, 19.7 g of 85% phosphoric acid and 600 mL of water were mixed. To the phosphate buffer was added 100 g of aminomalonamide, and a solution of 34.2 g of sodium hydroxide in 105 mL of water and 130 g of a 40% aqueous glyoxal solution were simultaneously added at 20 to 30° C. over 1 hour, and the reaction mixture was stirred at that temperature for 30 minutes. To the reaction mixture was added 25 mL of concentrated hydrochloric acid, and the reaction mixture was heated to 85° C., and then 60 mL of concentrated hydrochloric acid was added, and the reaction mixture was cooled to 15° C. A solid was collected by filtration to obtain 118 g of 3-hydroxy-2-pyrazinecarboxamide (compound C) as a brown solid.

Figure 9:
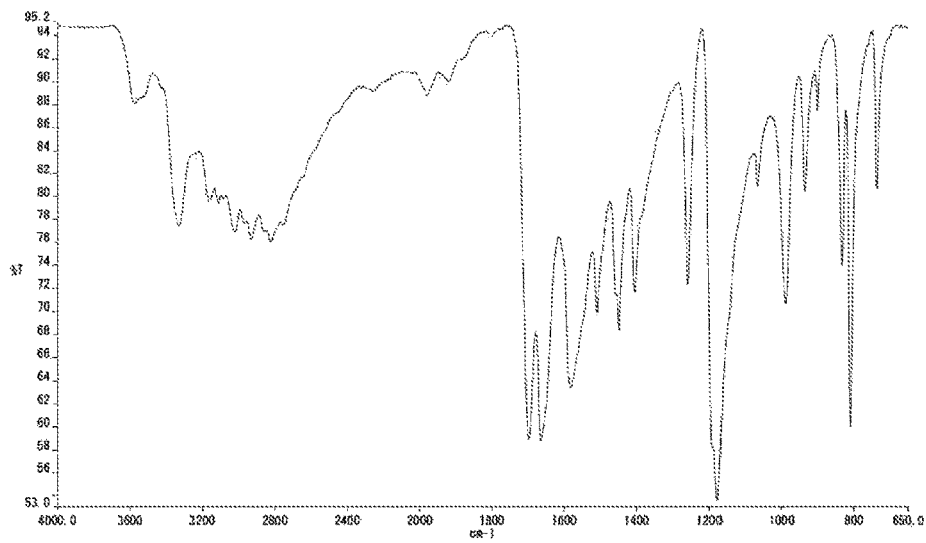
FIG. 9 illustrates one example of the infrared absorption spectrum (ATR method) of a hydrate of compound C.
Figure 10:
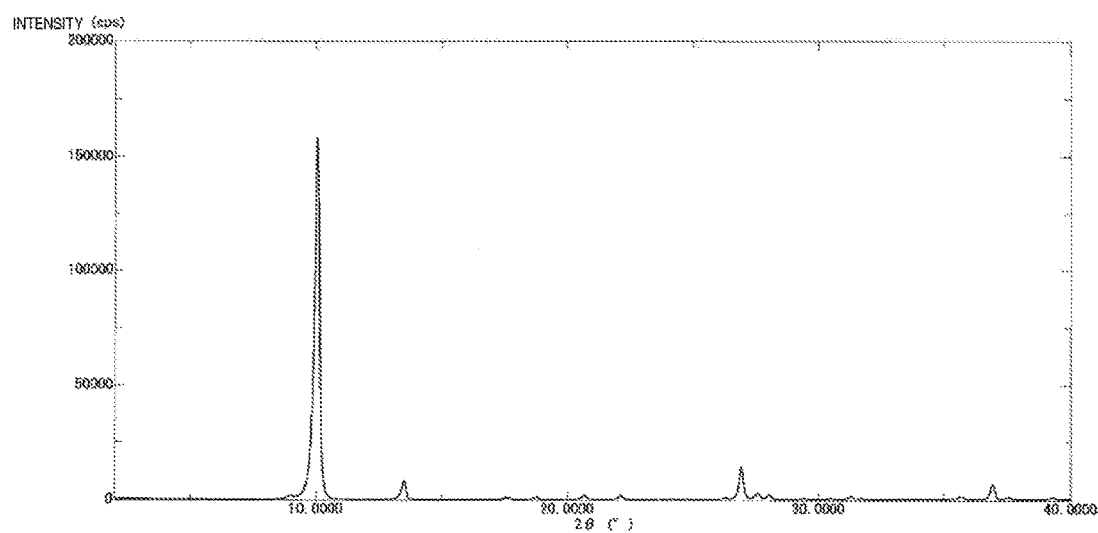
FIG. 10 illustrates one example of the powder X-ray diffraction pattern of a hydrate of compound C.

The resulting compound C was a hydrate.
Water content: 8.5%
$^1$H-NMR (DMSO-$d_6$) δ: 7.88-8.10 (3H, m), 8.69 (1H, s).
The infrared absorption spectrum is illustrated in FIG. 9.
The powder X-ray diffraction pattern is illustrated in FIG. 10 and the results are shown in Table 4.

TABLE 4

| 2θ (°) | d Value (Å) | Relative intensity (%) |
|---|---|---|
| 10.0 | 8.8 | 100 |
| 13.5 | 6.6 | 6 |
| 26.9 | 3.3 | 10 |

REFERENCE EXAMPLE 2

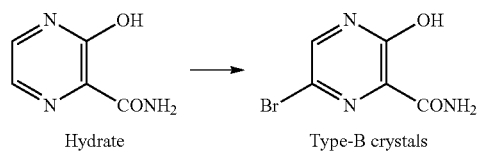 [SMILES: NC(=O)c1nccnc1O ; NC(=O)c1nc(Br)cnc1O]
Hydrate          Type-B crystals

The Example was performed according to the method in Example 1 of Patent Document 3.

To a suspension of 30.0 g of compound C obtained in Reference Example 1 in 75 mL of N,N-dimethylformamide was added 28.3 g of pyridine, and then 41.4 g of bromine was added at 80 to 100° C. and the reaction mixture was stirred at that temperature for 3 hours. To the reaction mixture were added 15 mL of toluene and 120 mL of water at 60 to 70° C., and the reaction mixture was cooled to 10° C. A solid was collected by filtration to obtain 30.5 g (purity: 99.4%) of type-B crystals of compound D as a brown solid.
$^1$H-NMR (CDCl$_3$) δ: 7.88-8.10 (3H, m), 8.69 (1H, s).

The infrared absorption spectrum and the powder X-ray diffraction pattern were similar to those in Example 3.

The content ratio of compound C included in the type-B crystals of compound D was measured by HPLC. The content ratio of compound C was 5039 ppm.

EXAMPLE 1

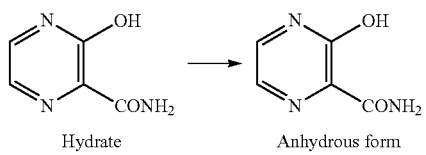 [SMILES: NC(=O)c1nccnc1O ; NC(=O)c1nccnc1O]
Hydrate          Anhydrous form

A mixture of 10.0 g of a hydrate of compound C obtained by the method described in Reference Example 1, 9.2 mL of pyridine and 24 mL of N,N-dimethylformamide was stirred at 70° C. for 1 hour. The reaction mixture was cooled to room temperature, and a solid was collected by filtration to obtain 8.5 g of an anhydrous form of compound C.

Figure 7:
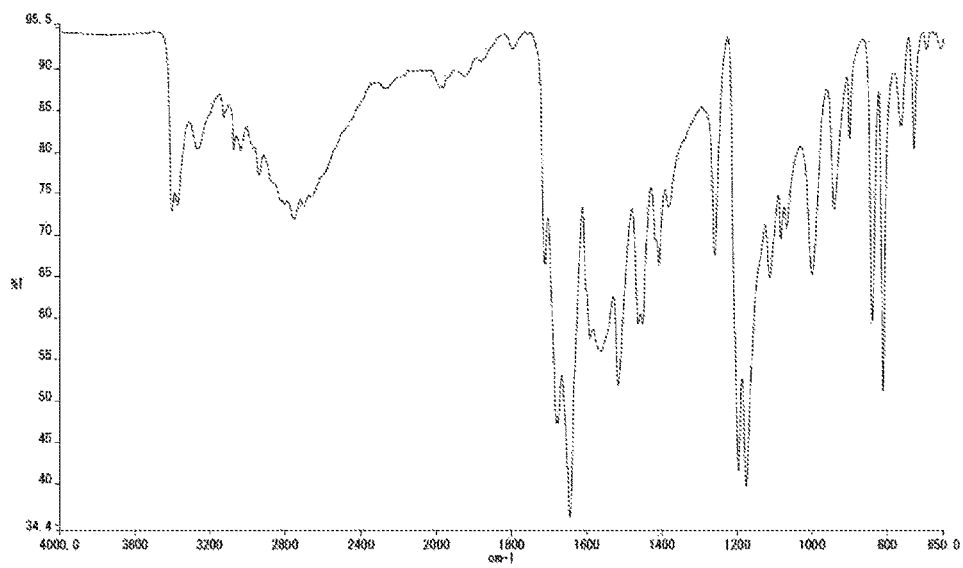
FIG. 7 illustrates one example of the infrared absorption spectrum (ATR method) of an anhydrous form of compound C.
Figure 8:
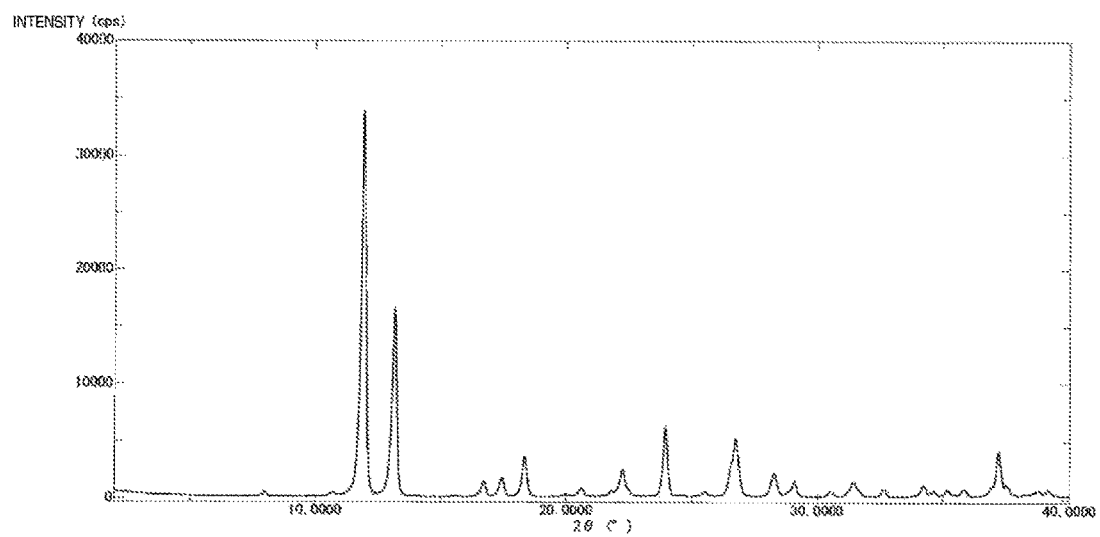
FIG. 8 illustrates one example of the powder X-ray diffraction pattern of an anhydrous form of compound C.

Water content: 0.12%
The infrared absorption spectrum is illustrated in FIG. 7.
The powder X-ray diffraction pattern is illustrated in FIG. 8 and the results are shown in Table 5.

TABLE 5

| 2θ (°) | d Value (Å) | Relative intensity (%) |
|---|---|---|
| 11.9 | 7.4 | 100 |
| 13.2 | 6.7 | 50 |
| 23.9 | 3.7 | 20 |
| 26.7 | 3.3 | 16 |

EXAMPLE 2

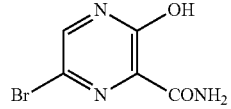
Type-A crystals

To a suspension of 20.0 g of type-B crystals of compound D obtained by the method described in Reference Example 2 in 50 mL of N,N-dimethylformamide was added 0.2 g of activated carbon at 50° C., and the reaction mixture was stirred at that temperature for 30 minutes. The insoluble fraction was filtered off at that temperature, and the filter cake was washed with 10 mL of N,N-dimethylformamide. The filtrate and the wash liquid were combined, 60 mL of water was added at 50° C., and thereafter the resulting mixture was cooled to 10° C. over 1 hour and 30 minutes. A solid was collected by filtration to obtain 17.3 g of type-A crystals of compound D.

The content ratio of compound C included in the type-A crystals of compound D was measured by HPLC. The content ratio of compound C was 54 ppm.

The infrared absorption spectrum is illustrated in FIG. 1.

Figure 2:
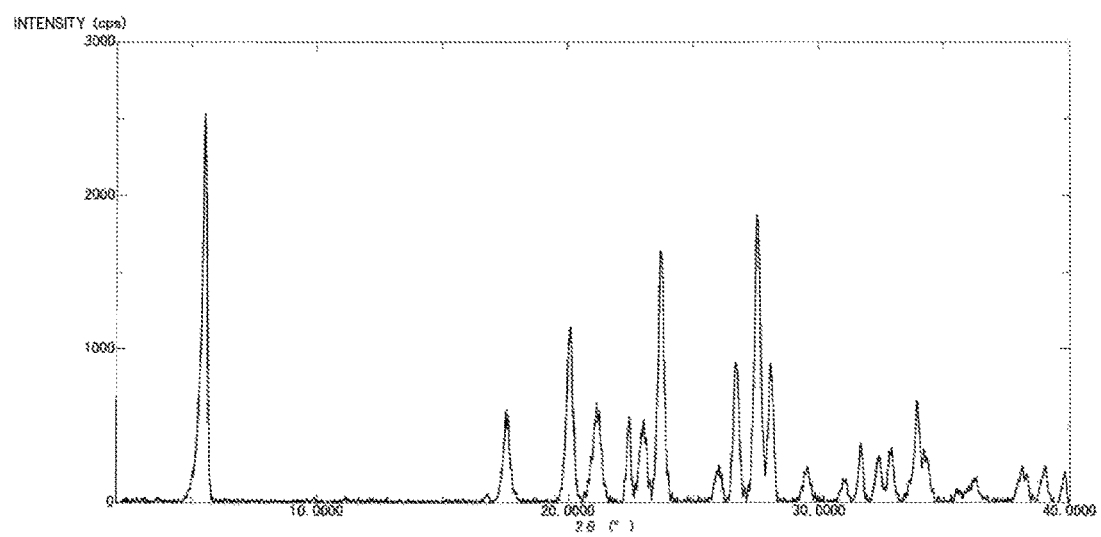
FIG. 2 illustrates one example of the powder X-ray diffraction pattern of type-A crystals of compound D.

The powder X-ray diffraction pattern is illustrated in FIG. 2 and the results are shown in Table 6.

TABLE 6

| 2θ (°) | d Value (Å) | Relative intensity (%) |
|---|---|---|
| 5.5 | 15.9 | 100 |
| 20.1 | 4.4 | 47 |
| 23.7 | 3.8 | 65 |
| 26.7 | 3.3 | 37 |
| 27.5 | 3.2 | 76 |
| 28.1 | 3.2 | 37 |

EXAMPLE 3

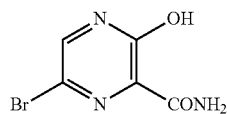
Type-B crystals

To a suspension of 20.0 g of type-B crystals of compound D obtained by the method described in Reference Example 2 in 50 mL of N,N-dimethylformamide was added 1.0 g of activated carbon at 50° C., and the reaction mixture was stirred at that temperature for 40 minutes. The insoluble fraction was filtered off at that temperature, and the filter cake was washed with 10 mL of N,N-dimethylformamide. The filtrate and the wash liquid were combined, 60 mL of water was added at 50° C., and thereafter the resulting mixture was cooled to 10° C. over 1 hour and 30 minutes. A solid was collected by filtration to obtain 18.4 g of type-B crystals of compound D.

The content ratio of compound C included in the type-B crystals of compound D was measured by HPLC. The content ratio of compound C was 1164 ppm.

Figure 3:
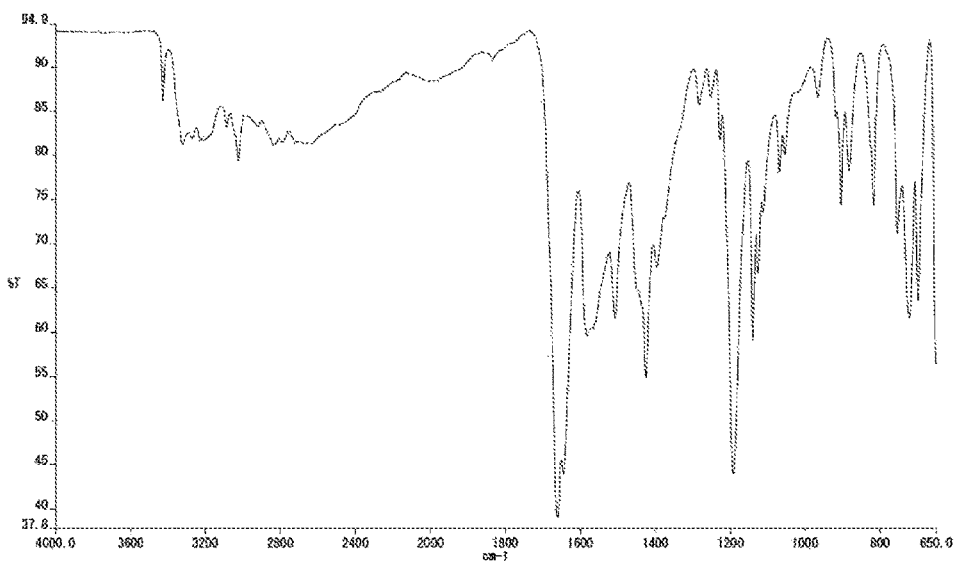
FIG. 3 illustrates one example of the infrared absorption spectrum (ATR method) of type-B crystals of compound D.

The infrared absorption spectrum is illustrated in FIG. 3.

Figure 4:
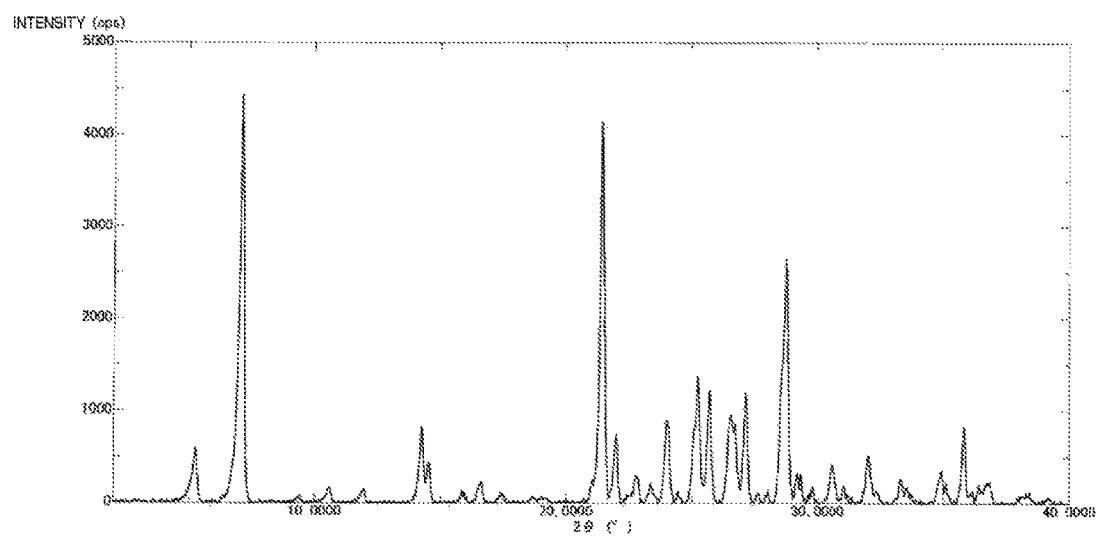
FIG. 4 illustrates one example of the powder X-ray diffraction pattern of type-B crystals of compound D.
Figure 5:
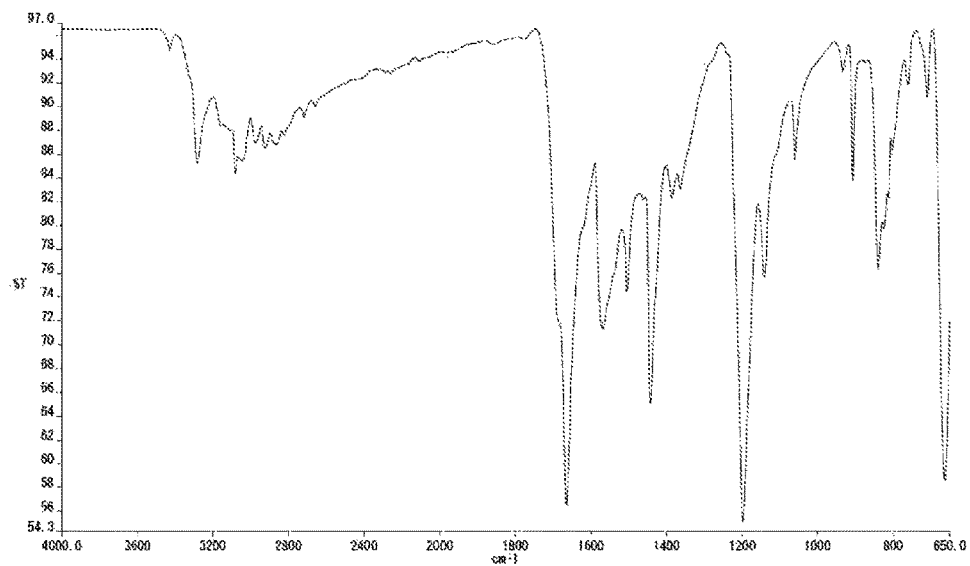
FIG. 5 illustrates one example of the infrared absorption spectrum (ATR method) of type-C crystals of compound D.
Figure 6:
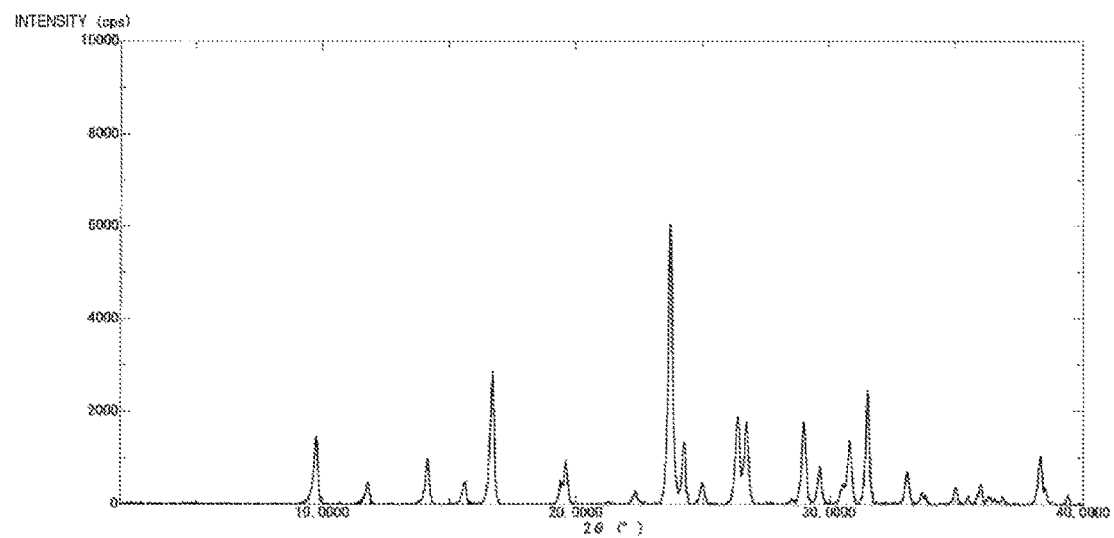
FIG. 6 illustrates one example of the powder X-ray diffraction pattern of type-C crystals of compound D.

The powder X-ray diffraction pattern is illustrated in FIG. 4 and the results were shown in Table 7.

TABLE 7

| 2θ (°) | d Value (Å) | Relative intensity (%) |
|---|---|---|
| 7.1 | 12.5 | 100 |
| 21.4 | 4.1 | 93 |
| 25.2 | 3.5 | 31 |
| 25.7 | 3.5 | 28 |
| 27.1 | 3.3 | 27 |
| 28.8 | 3.1 | 59 |

EXAMPLE 4

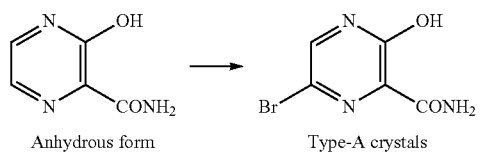 [SMILES: NC(=O)c1nccnc1O ; NC(=O)c1nc(Br)cnc1O]
Anhydrous form → Type-A crystals

To a suspension of 101 g of an anhydrous form of compound C in 253 mL of N,N-dimethylformamide was added 91.9 g of pyridine, and then 142 g of bromine was added at 65 to 88° C. and stirred at that temperature for 1 hour and 30 minutes. The reaction mixture was divided into five portions. To one of the portions was added 100 mL of toluene at 70 to 75° C., and then 80 mL of water was added thereto at 38 to 45° C., and the resulting mixture was cooled to 10° C. A solid was collected by filtration to obtain 26.1 g of type-A crystals of compound D as a brown solid.

The infrared absorption spectrum and the powder X-ray diffraction pattern were similar to those in Example 2.

The content ratio of compound C included in the type-A crystals of compound D was measured by HPLC. The content ratio of compound C was less than 100 ppm.

EXAMPLE 5

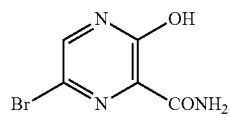
Type-B crystals

To a suspension of 26.1 g of type-A crystals of compound D obtained by the method described in Example 4 in 120 mL of water was added 12 mL of a 25% aqueous sodium hydroxide solution at room temperature. To the reaction mixture was added 1.00 g of activated carbon, and the reaction mixture was stirred at 60 to 65° C. for 45 minutes. The insoluble fraction was filtered off, and thereafter 8.2 mL of hydrochloric acid was added thereto at 60 to 63° C. The reaction mixture was cooled to room temperature, and stirred at 2 to 10° C. for 1 hour. A solid was collected by filtration to obtain 19.2 g of type-B crystals of compound D.

The infrared absorption spectrum and the powder X-ray diffraction pattern were similar to those in Example 3.

The content ratio of compound C included in the type-B crystals of compound D was measured by HPLC. The content ratio of compound C was less than 50 ppm.

EXAMPLE 6

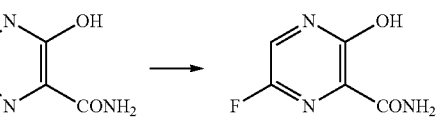

Type-A crystals of compound D obtained by the method described in Example 2 were used to provide 6-fluoro-3-hydroxy-2-pyrazinecarboxamide (compound A) according to the methods described in JP 5550347 B and JP 5559604 B.

The content ratio of compound C included in resulting compound A was less than 5 ppm.

INDUSTRIAL APPLICABILITY

The method for producing 6-bromo-3-hydroxy-2-pyrazinecarboxamide is useful as a method for producing a raw material for the production of 6-fluoro-3-hydroxy-2-pyrazinecarboxamide having an extremely low content ratio of impurities.

The invention claimed is:

1. A type-B crystal of 6-bromo-3-hydroxy-2-pyrazinecarboxamide having powder X-ray diffraction angles (2θ) of 7.1°, 21.4°, 25.2°, 25.7°, 27.1° and 28.8°.

2. A method for producing a type-B crystal of 6-bromo-3-hydroxy-2-pyrazinecarboxamide, wherein the method comprises:
   reacting a type-A crystal of 6-bromo-3-hydroxy-2-pyrazinecarboxamide having powder X-ray diffraction angles (2θ) of 5.5°, 20.1°, 23.7°, 26.7°, 27.5° and 28.1° with a base, to produce a salt of the type-A crystal of 6-bromo-3-hydroxy-2-pyrazinecarboxamide; and
   reacting the salt of the type-A crystal of 6-bromo-3-hydroxy-2-pyrazinecarboxamide with an acid, to produce a type-B crystal of 6-bromo-3-hydroxy-2-pyrazinecarboxamide having powder X-ray diffraction angles (2θ) of 7.1°, 21.4°, 25.2°, 25.7°, 27.1° and 28.8°.

3. The method of claim 2, wherein the base is selected from the group consisting of sodium hydroxide, sodium hydrogen carbonate and potassium hydroxide, and a combination thereof.

4. The method of claim 2, wherein the acid is selected from the group consisting of hydrochloric acid, nitric acid and sulfuric acid, and a combination thereof.

* * * * *